(12) United States Patent
Saito

(10) Patent No.: US 8,240,220 B2
(45) Date of Patent: Aug. 14, 2012

(54) METHOD FOR EVALUATING KNEADED CLAY, AND METHOD FOR MANUFACTURING KNEADED CLAY

(75) Inventor: Takao Saito, Nagoya (JP)

(73) Assignee: NGK Insulators, Ltd., Nagoya (JP)

( * ) Notice: Subject to any disclaimer, the term of this patent is extended or adjusted under 35 U.S.C. 154(b) by 264 days.

(21) Appl. No.: 12/706,879

(22) Filed: Feb. 17, 2010

(65) Prior Publication Data

US 2010/0227755 A1    Sep. 9, 2010

(30) Foreign Application Priority Data

Mar. 9, 2009   (JP) ................................. 2009-054443

(51) Int. Cl.
*G01N 33/00*   (2006.01)
(52) U.S. Cl. .......................................... 73/866; 73/432.1
(58) Field of Classification Search ................... 73/866, 73/432.1, 760
See application file for complete search history.

(56) References Cited

U.S. PATENT DOCUMENTS

| | | | | |
|---|---|---|---|---|
| 6,005,389 A | * | 12/1999 | Prammer | 324/303 |
| 6,097,271 A | * | 8/2000 | Kozakoff | 333/204 |
| 6,329,465 B1 | * | 12/2001 | Takahashi et al. | 525/191 |
| 7,252,135 B2 | * | 8/2007 | Noguchi et al. | 164/97 |
| 7,960,473 B2 | * | 6/2011 | Kobayashi et al. | 525/92 B |

FOREIGN PATENT DOCUMENTS

| | | |
|---|---|---|
| EP | 1 900 488 A1 | 3/2008 |
| JP | 09-033420 A1 | 2/1997 |
| JP | 2000-302525 A1 | 10/2000 |
| JP | 2001-106728 A1 | 4/2001 |
| JP | 4108648 B2 | 4/2008 |

OTHER PUBLICATIONS

K. Peter C. Vollhardt et al., *Organic Chemistry, Structure and Function*, (vol. One), Fourth Edition, "*Chapter 10: Structure Determination by NMR Spectroscopy*", 2003, pp. 419-478.

J. Fripiat, et al., "*Thermodynamic and Microdynamic Behavior of Water in Clay Suspensions and Gels*," Journal of Colloid and Interface Science, vol. 89, No. 2, Oct. 1982, pp. 378-400.

* cited by examiner

*Primary Examiner* — Max Noori
(74) *Attorney, Agent, or Firm* — Burr & Brown

(57) ABSTRACT

A method of evaluating kneaded clay includes, preparing kneaded clay by mixing and kneading at least ceramic raw material and water as contained materials, measuring T1 relaxation time and/or T2 relaxation time of proton contained in the contained materials by NMR method, and evaluating a kneaded state of the kneaded clay. There is further provided a method for manufacturing kneaded clay, wherein the kneaded clay is kneaded by using the method for evaluating kneaded clay while checking the kneaded state.

7 Claims, 6 Drawing Sheets

METHOD FOR EVALUATING KNEADED CLAY, AND METHOD FOR MANUFACTURING KNEADED CLAY

BACKGROUND OF THE INVENTION

The present invention relates to a method for evaluating kneaded clay used for manufacturing a ceramic structure used for a filter, a catalyst carrier, an electric transmission insulator, a refractory, or the like and to a method for manufacturing kneaded clay.

Ceramics, which are inorganic materials, have excellent physical, chemical, and electrical characteristics which metals and organic materials do not have. Further, ceramics have an advantage that any shape can be obtained from the raw material, and an example representing this is a honeycomb structure constituted of thin walls of some microns.

Generally, a ceramic structure is manufactured through a step of preparing kneaded clay from a mixed raw material containing a ceramic raw material, an organic binder, and/or an inorganic binder, a step of manufacturing a formed body by forming the kneaded clay into a desired shape, a step of drying the formed body, and the step of firing a formed article to obtain a fired article in this order.

The kneaded clay is prepared by mixing and kneading contained materials such as a ceramic raw material, a binder, and a solvent. The nature of the kneaded clay significantly influences on the characteristics of the ceramic structure. For example, when the kneaded clay is prepared with contained materials such as a ceramic raw material, a binder, and a solvent being insufficiently kneaded, there is caused variance in a strength characteristic and an elastic characteristic of a formed article obtained from the kneaded clay. Therefore, in the preparation of the kneaded clay, it is desirable that the degree of kneading of the contained materials is grasped by an objective index.

The characteristics regarding the transformability, shape-retentivity, and flowability of kneaded clay, that is, so-called rheological properties of kneaded clay significantly influence on the shape-retentivity of the formed article manufactured with the kneaded clay. For example, in the case that a ceramic formed article is manufactured by subjecting kneaded clay to extrusion forming, when flowability of the kneaded clay is poor, the kneaded clay is pressure-bonded to the die for extrusion to generate a cut or a fine on a surface of the resultant formed article. On the other hand, when the flowability of the kneaded clay is good, the formed article manufactured by extrusion forming may easily be deformed.

Thus, though the nature of kneaded clay is important, in an actual production site, the evaluation on the nature of kneaded clay depends on operator's proficient senses of vision, touch, and the like. However, by the evaluation of the nature of kneaded clay due to operator's senses, it is difficult to stably manufacture kneaded clay having high quality. In addition, the acquisition of the skill to recognize good nature of kneaded clay by senses of vision, touch, and the like needs persistent trial and error and training. Even if the skill is acquired through a great deal of effort, it is difficult to hand the skill on to another operator. Therefore, the nature of kneaded clay, which has been recognized as good by an operator's senses, has been tried to grasp by an objective index by a scientific measurement means.

JP-A-9-33420 discloses a method for evaluating a kneaded state of an inorganic powder represented by a ceramic powder and an organic binder by observation with a transmission electron microscope. In this method, by observing the thickness of an organic binder membrane on the surface of the inorganic powder formed by kneading, the degree of kneading of the inorganic powder and an organic binder is evaluated.

JP-A-2000-302525 discloses a method for manufacturing kneaded clay, showing a method for evaluating rheological properties of kneaded clay by an elasticity test and a capillary rheometer test. From the evaluation, it has been found that rheological properties of kneaded clay is significantly influenced by the addition proportion of a binder, a surfactant, and water added to a ceramic raw material.

Nuclear magnetic resonance (NMR) is an indispensable tool for determining a structure of an organic compound as introduced in the "Organic Chemistry" (Volume One), Fourth edition, by K. Peter C. Vollhardt, Neil E. Schore, Chemical Coterie, Chapter 10: Structure Determination by NMR Spectroscopy, Pages 419 to 478, since the state of molecules can be observed based on the energy absorption/ejection phenomenon of nuclear spin. In addition, NMR is used as a tool for grasping the nature of a material containing an organic compound as the main component. For example, JP-A-2001-106728 discloses that a water-absorbing resin excellent in water absorbability can be obtained by specifying the degree of cross-linkage of a resin by the T2 relaxation time of $^1$H-NMR. Further, Japanese Patent No. 4108648 discloses a method for manufacturing a carbon fiber composite material by the use of the T2 relaxation time of $^1$H-NMR in order to grasp the state of dispersion of resin in a mixed material. In this method, there is specified a uniform dispersion state of a carbon fiber composite material containing a thermosetting resin, carbon nanofibers, and particles for dispersion.

In the medical diagnosis field, a magnetic resonance imaging method (MRI) where the principle of the NMR is applied has already been used. The MRI uses that the state of water molecules occupying most of a human body is reflected on the proton relaxation time. It is expected that NMR will take one step further from the medical diagnosis field to the production field, in particular, to quality control in a factory or the like.

As a matter of course, the state of clay cannot be grasped accurately even by a method disclosed in JP-A-9-33420 or a method disclosed in JP-A-2000-302525. This is because the senses such as vision and touch of a proficient operator comprehensively catch very complex and miscellaneous factors. In order to grasp the state of clay, it is necessary to decompose the complex and miscellaneous factors, investigate decomposed individual factors based on multilateral indexes, and further investigate the integration of the evaluation data regarding the individual factors. Therefore, still desired are search of unknown factors required for grasping the state of kneaded clay and an evaluation method therefor.

As in JP-A-2001-106728 and Japanese Patent No. 4108648, NMR is a powerful tool in analysis of an organic compound and is widely applied to production of a chemical product containing an organic compound such as resins as the main component. However, there is a barrier against expansion of application to another technical field. For example, it is known that, in accordance with progress of kneading, the binder is sheared to lower the molecular amount and to cause a change in a degree of adhesion of water to the ceramic raw material. Therefore, even if NMR is applied to evaluation of a degree of kneading, enormous knowledge and an operator's proficient skills described above are necessary for selection of a phenomenon measured by NMR and construal of the measurement results.

SUMMARY OF THE INVENTION

In view of the aforementioned problems, the present invention aims to provide a method for evaluating kneaded clay to evaluate the nature of the kneaded clay by an objective index, and the method for manufacturing kneaded clay enables to manufacture kneaded clay while checking the kneaded state of the kneaded clay by an objective index.

In order to solve the aforementioned problems, the present inventors keenly investigated knowledge regarding ceramic technology, which took a long while to cultivate, again from the scientific viewpoint and found out that kneaded state of the kneaded clay can be evaluated by NMR, which led to the completion of the present invention. That is, according to the present invention, there is provided the following method for evaluating kneaded clay and method for manufacturing kneaded clay.

[1] A method of evaluating kneaded clay which comprises: preparing kneaded clay by mixing and kneading at least ceramic raw material and water as contained materials, measuring T1 relaxation time and/or T2 relaxation time of proton contained in the contained materials by NMR method, and evaluating a kneaded state of the kneaded clay.

[2] A method for evaluating kneaded clay according to [1], wherein a signal for measuring the T1 relaxation time and/or the T2 relaxation time of the proton contained in the contained materials has the signal sent from the proton of the water as the main component.

[3] A method for evaluating kneaded clay according to [1] or [2], wherein the kneaded clay is for subjecting, after the kneading, to a forming step, a drying step, and a firing step.

[4] A method for evaluating kneaded clay according to [3], wherein the kneaded clay has a cordierite composition or an alumina composition after the firing step.

[5] A method for manufacturing kneaded clay which comprises: using a method for evaluating kneaded clay according to any one of [1] to [4], and kneading the kneaded clay while checking the kneaded state of the kneaded clay by the T1 relaxation time and/or the T2 relaxation time of the proton contained in the contained materials.

[6] A method for manufacturing kneaded clay according to [5], wherein the kneaded clay is kneaded until the T1 relaxation time, measured at magnetostatic field strength of 0.3 to 9.4 T, of the proton contained in the contained materials becomes 80% or less of the initial value before kneading.

In a method for evaluating kneaded clay of the present invention, the state of contained materials, for example, the state of water molecules in the kneaded clay is scientifically observed to evaluate the nature of the kneaded clay by an objective index. In a method for manufacturing kneaded clay of the present invention, kneaded clay can be manufactured while checking the kneaded state of the kneaded clay by an objective index.

REFERENCE NUMERALS

Figure 1:
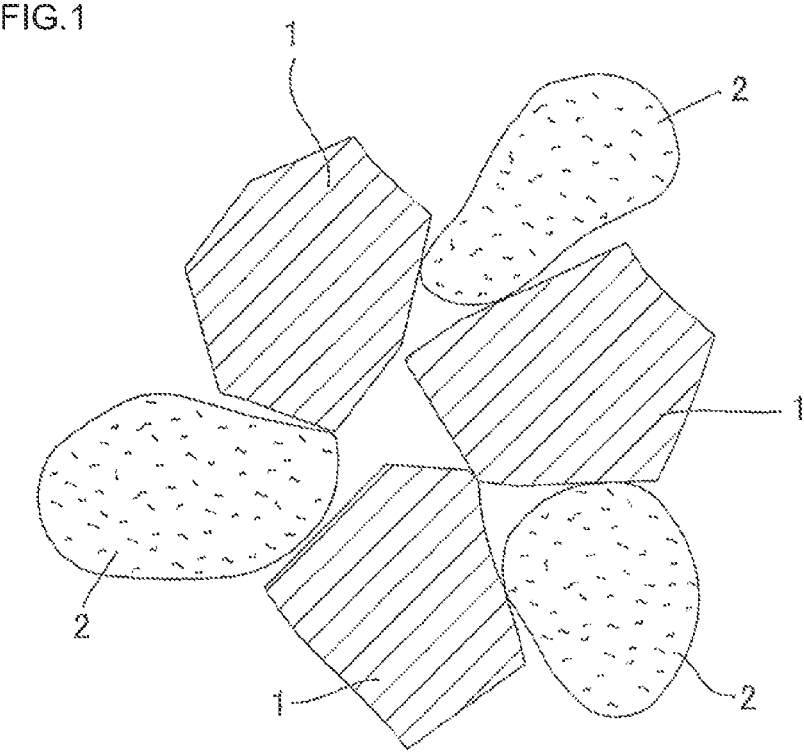
FIG. 1 is a view schematically showing a kneaded state of ceramic raw material particles and water right after the kneading is started.

1: Ceramic raw material particle, 2: Water

DETAILED DESCRIPTION OF THE INVENTION

Hereinbelow, an embodiment of the present invention will be described with referring to drawings. The present invention is by no means limited to the following embodiment, and changes, modifications, improvements can be made as long as they do not deviate from the scope of the present invention.

1. Method for Evaluating Kneaded Clay:

1-1. Summary of a Method for Evaluating Kneaded Clay of the Present Invention:

In a method for evaluating kneaded clay of the present invention, the nature of kneaded clay is evaluated on the basis of the proton relaxation time measured by the NMR method, for example, an objective index obtained from a proton relaxation time measurement method using a NMR device. Though the method is called NMR method in the present specification, it may be called a nuclear magnetic resonance method, MR method, or MR(I) method. Also, regarding the relaxation time indication, the T1 relaxation time may be indicated as a longitudinal relaxation time, and the T2 relaxation time may be indicated as a transverse relaxation time. In addition, by integrating the T1 relaxation time or the T2 relaxation time for each site in a two-dimensional plane of a cross section to express the difference in relaxation time by the contrast, distribution in the plane (imaging) can be obtained.

In the first place, "kneaded clay" here is prepared by mixing contained materials such as a ceramic raw material, a binder, and solvent and kneading them. The kneaded clay may be expressed as clay. The kneaded clay is preferably kneaded clay with which a ceramic structure can be manufactured by forming the clay into a predetermined shape, followed by drying and firing. Examples of such kneaded clay include kneaded clay whose material composition after firing becomes a cordierite composition or an alumina composition. Incidentally, in the present specification, even in the case that the appearance of kneaded clay is not in a clay-like state, the mixture of contained materials such as a ceramic raw material, a binder, and a solvent is called as kneaded clay.

In a method for evaluating kneaded clay of the present invention, a relaxation time measurement method using a NMR device is used to measure the T1 relaxation time and/or the T2 relaxation time of the proton contained in the contained materials in the kneaded clay.

1-2. Relation Between the Kneaded State of Kneaded Clay and the Relaxation Time of the Proton Contained in the Contained Materials in the Kneaded Clay:

The T1 relaxation time and the T2 relaxation time of the proton contained in the contained materials in kneaded clay reflect the state of the contained materials in the kneaded clay at a micro level or molecular level. In a method for evaluating kneaded clay of the present invention, the state at a molecule level of the contained materials where kneading of the kneaded clay changes in accordance with the progress of kneading is distinguished by means of change in the T1 relaxation time and the T2 relaxation time of the proton contained in the contained materials in the kneaded clay.

1-3. The Case that a Signal for Measuring the Relaxation Time has the Signal Sent from the Proton Contained in Water as the Main Component:

In a method for evaluating kneaded clay of the present invention, the kneaded clay to be evaluated is suitably kneaded clay where a signal for measuring the T1 relaxation time and/or the T2 relaxation time of the proton contained in the contained materials in the kneaded clay has the signal sent from the proton of the water as the main component. This is because the dynamics of the T1 relaxation time and the T2 relaxation time of the proton contained in the contained materials in the kneaded clay can be considered to be almost the same as that of the T1 relaxation time and/or the T2 relaxation time of the proton contained in the water in the kneaded clay. Generally, in the state that water molecules adhere to the surface of the materials, the T1 relaxation time and the T2 relaxation time of the proton contained in the water become short. In contrast, in the state that water molecules can move freely as a mass of liquid water, the T1 relaxation time and the T2 relaxation time of the proton contained in the water become long. The phrase "a signal for measuring the T1 relaxation time and/or the T2 relaxation time of the proton has the signal sent from the water as the main component" means that the material having the highest inner addition rate (mass %) among the materials having a proton in the contained materials in kneaded clay is water.

FIG. 1 shows a state of kneaded clay right after the kneading is started, in particular, a state where ceramic raw material particles 1 and water 2 are mixed together. Right after the start of kneading, water is present in a state of a liquid mass at a high proportion. At this time, most of the water molecules can move freely, and the T1 relaxation time and the T2 relaxation time of the proton contained in water in the kneaded clay are long.

Figure 2:
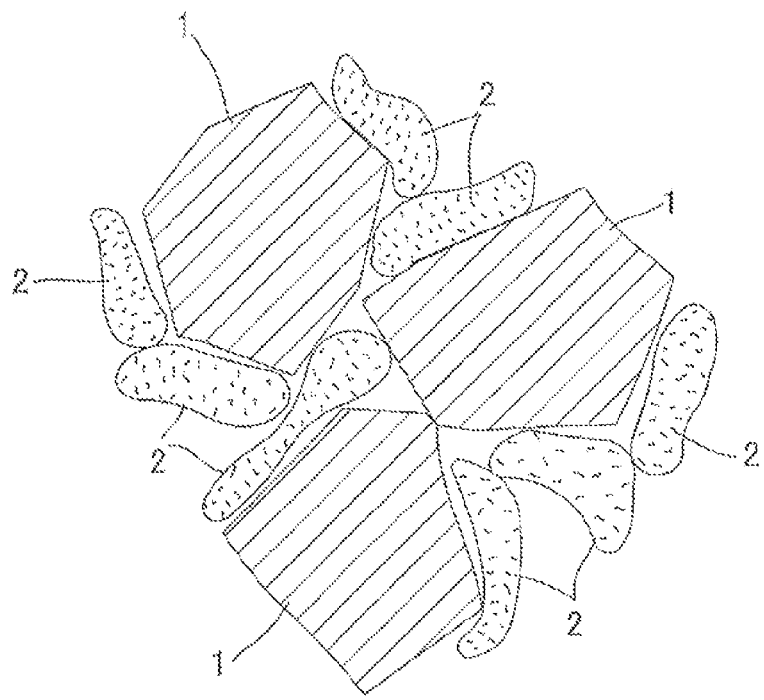
FIG. 2 is a view schematically showing a kneaded state of ceramic raw material particles and water during kneading, which follows FIG. 1.

FIG. 2 is a view schematically showing a kneaded state of ceramic raw material particles and water during kneading. The water 2 starts covering the surface of the ceramic raw material particles 1. Therefore, the amount of the water 2 adhering to the surface of the ceramic raw material particles 1 increases relatively, and the mass of water capable of moving freely decreases relatively. In accordance with the change in the state of the water molecules, the T1 relaxation time and the T2 relaxation time of the proton contained in the water in the kneaded clay are shortened in comparison with the time right after the start of kneading.

Figure 3:
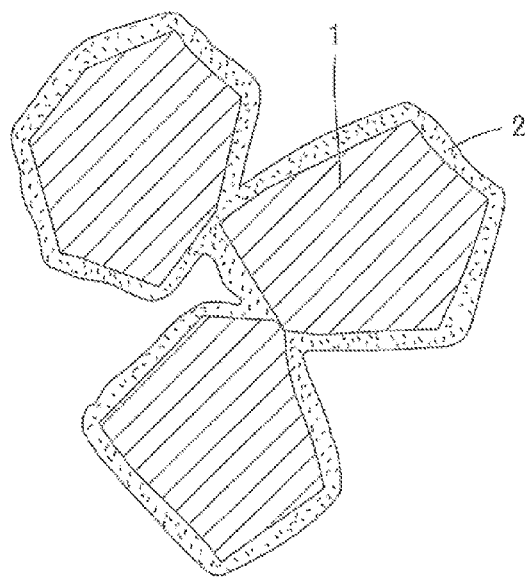
FIG. 3 is a view schematically showing a kneaded state of ceramic raw material particles and water after kneading, which follows FIG. 2.

FIG. 3 schematically shows a state of kneaded clay which was sufficiently kneaded. The water 2 covers the surfaces of the ceramic raw material particles 1 in a membrane state. At this time, since most of the water molecules adheres to the surfaces of the ceramic raw material particles 1, the T1 relaxation time and the T2 relaxation time of the proton contained in the water in the kneaded clay become shorter. That is, a method for evaluating kneaded clay of the present invention utilizes the phenomenon that the T1 relaxation time and/or the T2 relaxation time of the proton contained in water in the kneaded clay becomes short in accordance with the dispersion of water in kneaded clay with the kneaded clay being sufficiently kneaded in the case that a signal for measuring the T1 relaxation time and/or the T2 relaxation time of the proton contained in the contained materials in the kneaded clay has the signal sent from the proton of the water as the main component.

Next, a description will be given regarding the case of measuring kneaded clay where a signal for measuring the T1 relaxation time and/or the T2 relaxation time of the proton contained in the contained materials has the signal sent from the proton of the water as the main component. In particular, a detailed description will be given regarding the relation between the T1 relaxation time and/or the T2 relaxation time of the proton contained in the contained materials in kneaded clay and water content or an organic binder.

1-3-1. Relation Between Water Content in Kneaded Clay and Relaxation Time of the Proton Contained in the Contained Materials in Kneaded Clay:

When the water content in kneaded clay is high, a signal for measuring the T1 relaxation time and/or the T2 relaxation time of the proton contained in the contained materials in the kneaded clay is more likely to have the signal sent from the proton of the water as the main component, and the transition of the T1 relaxation time and the T2 relaxation time of the proton contained in the contained materials in the kneaded clay furthermore reflects the transition of the T1 relaxation time and the T2 relaxation time of the proton contained in the water in the kneaded clay.

A description will be given with referring to FIG. 3. In the case that the water content in kneaded clay is high, when the kneaded clay is sufficiently kneaded, the water 2 covers the surfaces of the ceramic raw material particles 1 in a thick membrane form. In this thick membrane-like water 2, some water molecules adhere to the surfaces of the ceramic raw material particles 1, and the other water molecules can move freely. When the water content in the kneaded clay is high, since the membrane of the water 2 on the surfaces of the ceramic raw material particles 1 becomes thick to increase the proportion of the water molecules capable of moving freely, the T1 relaxation time and the T2 relaxation time of the proton contained in the contained materials in the kneaded clay after kneading become longer than in the case that the water content in the kneaded clay is low.

It should be noted that, in a method for evaluating kneaded clay of the present invention, even in the case that the water content in the kneaded clay is high, as the ceramic raw material particles and water are being kneaded, the water is dispersed in the kneaded clay, and the T1 relaxation time and the T2 relaxation time of the proton contained in the contained materials in the kneaded clay are getting shorter.

1-3-2. Relation Between Proportions of Organic Binder and Surfactant in Kneaded Clay and Relaxation Time of Proton Contained in Contained Materials:

The T1 relaxation time and the T2 relaxation time of the proton contained in the contained materials in the kneaded clay are influenced also by a signal from proton contained in an organic binder and a surfactant in the kneaded clay. Therefore, the T1 relaxation time and the T2 relaxation time of the proton contained in the contained materials in the kneaded clay have different values when the amounts and kinds of the organic binder and surfactant in the kneaded clay are different. In addition, actually, when the amounts and kinds of the organic binder and surfactant in the kneaded clay are different, the state of kneading is different. However, in kneaded clay where a signal for measuring the T1 relaxation time and/or the T2 relaxation time of the proton has the signal sent from the proton of the water as the main component, it can be considered that the transition of the T1 relaxation time and/or the T2 relaxation time of the proton contained in the contained materials reflects the change in the state of the water molecules in the kneaded clay almost precisely. In such kneaded clay, regardless of the amounts and kinds of the organic binder and surfactant, as the water is dispersed in accordance with the progress of the kneading of the kneaded clay, the T1 relaxation time and the T2 relaxation time of the proton contained in the contained materials are getting shorter.

2. Method for Manufacturing Kneaded Clay:

2-1. Summary of Method for Manufacturing Kneaded Clay of the Present Invention:

In a method for manufacturing kneaded clay of the present invention, the aforementioned method for evaluating kneaded clay is used. That is, in a method for manufacturing kneaded clay of the present invention, the kneaded clay is kneaded while checking the kneaded state of the kneaded clay by the T1 relaxation time and/or the T2 relaxation time of the proton contained in the contained materials in the kneaded clay.

As described above, the T1 relaxation time and/or the T2 relaxation time of the proton contained in the contained materials in the kneaded clay in a good kneaded state depends on the water content and the kinds and the amounts of the organic binder and the surfactant. Here, regarding "kneaded while checking the kneaded state of the kneaded clay", the specific embodiment differs depending on the case that the composition of the kneaded clay is known or not known. For example, in the case that kneaded clay having the same composition is already subjected to an evaluation test and that the T1 relaxation time and/or the T2 relaxation time of the proton contained in the contained materials in the kneaded clay in a kneaded state suitable for forming is grasped, only observation that the time reaches the relaxation time required is necessary. On the other hand, in the case that the T1 relaxation time and/or the T2 relaxation time of the proton contained in the contained materials in the kneaded clay in a kneaded state suitable for forming has not yet been grasped, the transition of the T1 relaxation time and/or the T2 relaxation time of the proton may be observed to continue kneading until the T1 relaxation time and/or the T2 relaxation time becomes sufficiently short to have a value where the T1 relaxation time and/or the T2 relaxation time becomes stable in the forming step.

Incidentally, the sample measured by the NMR method may appropriately be collected from the material before kneading, during kneading, and after kneading, and from a formed article (kneaded clay) formed into a desired shape before firing. There is no particular limitation on a method for kneading the kneaded material as long as the sample can be measured by the NMR method.

In particular, in a method for manufacturing kneaded clay of the present invention, it is preferable to knead the kneaded clay until the T1 relaxation time of the proton contained in the contained materials measured at a magnetostatic field strength of 0.3 to 9.4 T becomes 80% or less of the T1 relaxation time, i.e., initial value before kneading. "Before kneading" means the state where all the contained materials to be contained in the kneaded clay are mixed together. The step where all the contained materials are mixed together is called also a blending step, a mixing step, or a mixer step.

From the kneaded clay obtained by this manufacturing method, a honeycomb structure constituted of thin walls without a cut or a fine can be manufactured by extrusion forming

EXAMPLE

Hereinbelow, the present invention will be described in more detail on the basis of Examples. However, the present invention is by no means limited to these Examples.

3-1. Materials and Measuring Instrument:

3-1-1. Preparation of Kneaded Clay:

(1) Preparation of Mixed Raw Material

Examples 1 to 5

In Examples 1 to 5, the contained materials were a ceramic raw material, methyl cellulose used as the organic binder, potassium laurate used as the surfactant, and water. These contained materials were mixed to prepare a mixed raw material (Table 1). With respect to 100 parts by mass of the ceramic raw material were mixed 6 parts by mass of methyl cellulose as the organic binder, 1 part by mass of potassium laurate, and 29.5 to 35.0 parts by mass of water to prepare the mixed raw material. Incidentally, as a ceramic raw material of each of Examples 1 to 5, there was used a cordierite-forming raw material containing 42 mass % of talc, 43 mass % of kaolin, 14 mass % of at least one kind selected from alumina and aluminum hydroxide, and 1 mass % of silica.

TABLE 1

| | Composition of ceramic raw material | Organic binder (parts by mass)*[1] | Surfactant (parts by mass)*[1] | Water (parts by mass)*[1] | Test |
|---|---|---|---|---|---|
| Example 1 | Cordierite composition | 6.0 | 2.0 | 32.0 | Test 1 |
| Example 2 | Cordierite composition | 6.0 | 2.0 | 29.5 | Test 2 |
| Example 3 | Cordierite composition | 6.0 | 2.0 | 31.5 | |
| Example 4 | Cordierite composition | 6.0 | 2.0 | 34.0 | |
| Example 5 | Cordierite composition | 6.0 | 2.0 | 35.0 | |
| Example 6 | Alumina | 6.0 | 2.0 | 14.0 | Test 3 |
| Example 7 | Alumina | 3.0 | 2.0 | 14.0 | |
| Example 8 | Alumina | 6.0 | 4.0 | 14.0 | |

*[1]Value with respect to 100 parts by mass of ceramic raw material

Examples 6 to 8

In each of Examples 6 to 8, with respect to 100 parts by mass of alumina used as the ceramic raw material, 3 to 6 parts by mass of methyl cellulose as an organic binder, 2 to 4 parts by mass of potassium laurate as the surfactant, and 14 parts by mass of water were mixed to prepare a mixed raw material.

(2) Preparation of Kneaded Clay

The kneaded clay was prepared by subjecting 1.0 kg of the mixed raw material to kneading for 50 minutes by the use of a pressure kneader (trade name of TD1-3M Type Pressure Kneader produced by Toshin Co., Ltd.). Incidentally, the sample of the kneaded clay used for measurement by the NMR device was collected by 50 g from the time before kneading and every 10 minutes from the start of kneading. Therefore, collection of the kneaded clay was performed before kneading and 10 minutes, 20 minutes, 30 minutes, and 40 minutes after the start of kneading, and 50 minutes after the start of kneading (right after the completion of kneading). These kneaded clay samples were vacuum sealed under a condition of removing air with a resin film in order to avoid drying and degeneration and stored until the measurement by the NMR measurement device.

(3) Measurement of Water Content

Regarding the aforementioned kneaded clay samples, the water content was obtained by heating the samples right after the collection at 120° C. to measure the dry mass and dividing the mass of each of the samples before heating by the dry mass. In addition, the water content of each of the kneaded clay samples was shown by percentage of water content with respect to the mass of each of the samples before heating.

3-1-2. NMR Measurement Device:

As the NMR measurement device, there were used CompacTscan having a magnetostatic field intensity of 0.3 T produced by Magnetic Resonance Technology, LTD., and AVANCE having a magnetostatic field intensity of 9.4 T produced by BRUKER CORPORATION.

3-1-3. Measurement of Binder Molecular Weight:

For measurement of the binder molecular weight, GPC produced by TOSOH CORPORATION.

3-1-4. Extrusion Forming and Measurement of Extrusion Resistance:

Regarding the capillary rheometer test for extrusion resistance, a formed article obtained by preliminarily forming the kneaded clay into a cylindrical shape having a diameter of 25 mm and a height of 55 mm was inserted into a cylinder having a diameter of 25 mm, and then pressure was applied to the formed article to pass the formed article through a capillary having a diameter of 1.0 mm, a height of 20 mm, and a last edge of 0.1 mm in width times 2 mm provided at the bottom of the cylinder, thereby measuring the resistance value.

3-2. Evaluation Test Regarding Kneaded State, State of Water Molecule, State of Organic Binder, and Extrusion Forming:

(Test 1):

3-2-1. Kneaded State:

It was found by eye observation that the kneaded clay changes from a powdery form to a clayey form from 10 minutes to 20 minutes after the start of kneading.

3-2-2. Observation on Kneaded State Due to T1 Relaxation Time and T2 Relaxation Time of Proton:

The kneaded clay samples collected before kneading, 10 minutes, 20 minutes, 30 minutes, and 40 minutes after the start of kneading, and 50 minutes after the start of kneading (right after the completion of kneading) in the step of (2) of Example 1 were measured for the T1 relaxation time and the T2 relaxation time of the proton contained in the contained materials in the kneaded clay. The magnetostatic field intensity was 0.3 T.

Figure 4:
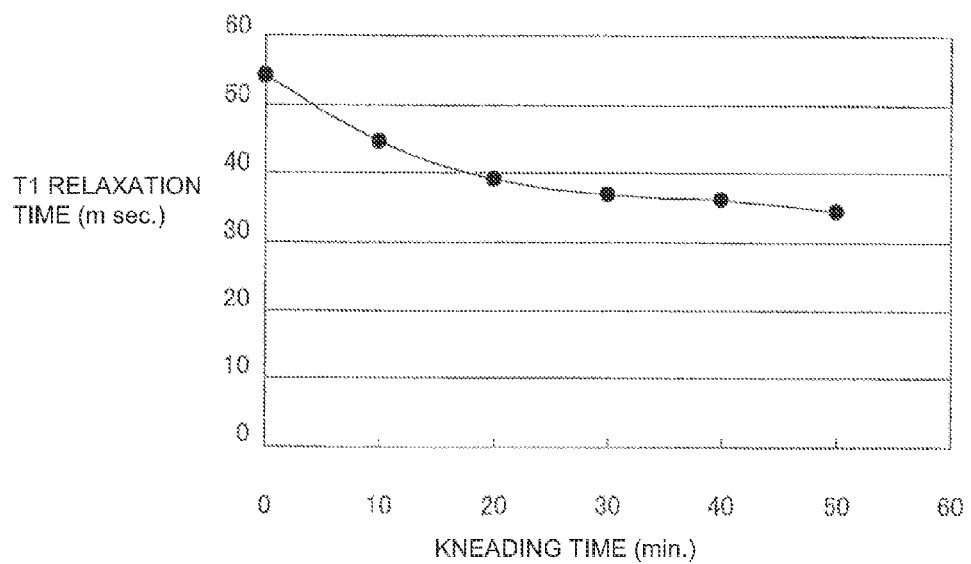
FIG. 4 is a line plot showing the transition of the T1 relaxation time of the proton contained in the contained materials in the kneaded clay of Example 1.
Figure 5:
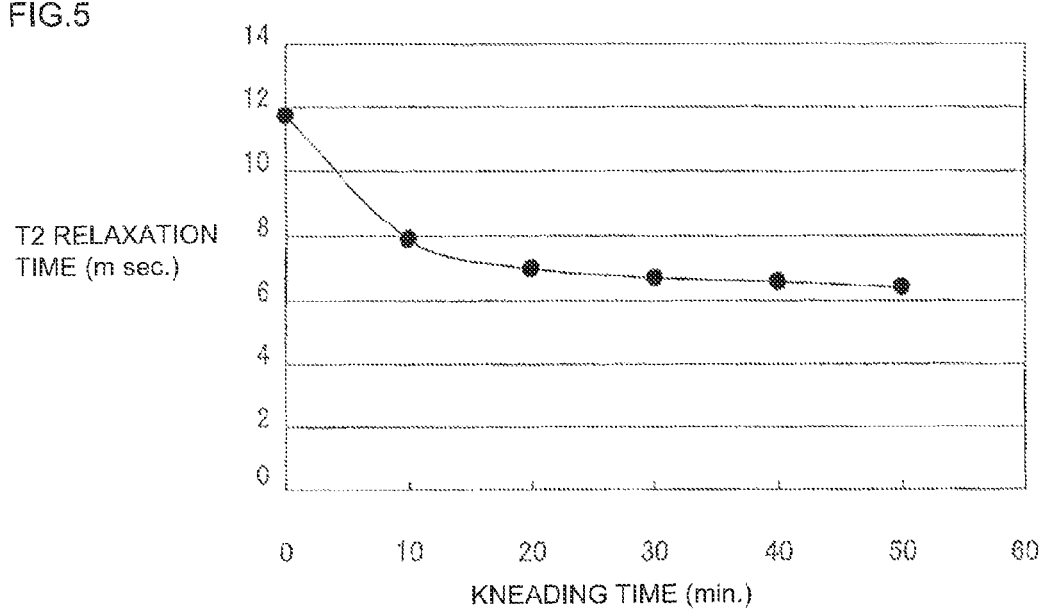
FIG. 5 is a line plot showing the transition of the T2 relaxation time of the proton contained in the contained materials in the kneaded clay of Example 1.
Figure 6:
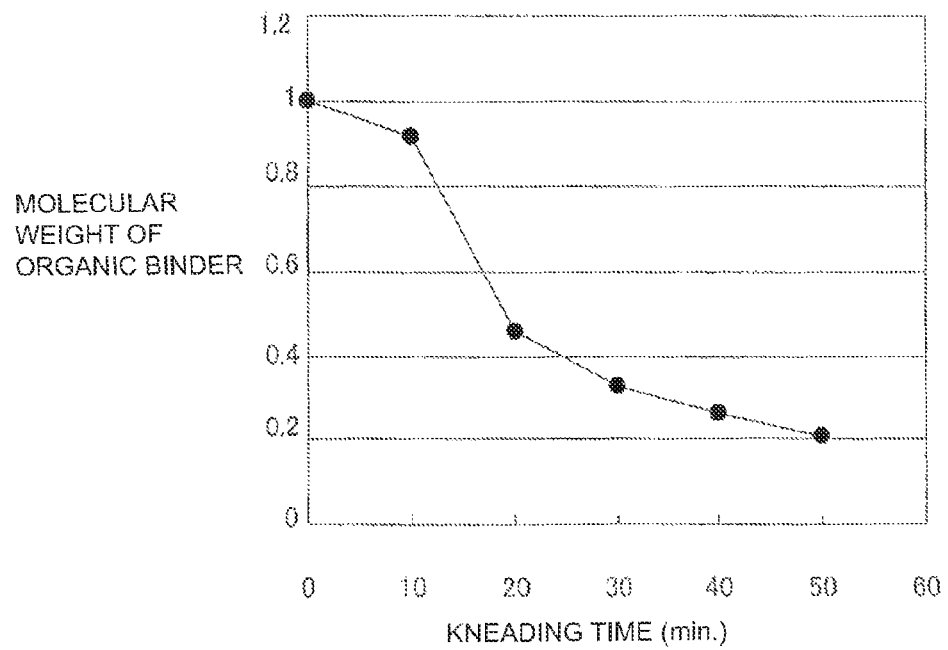
FIG. 6 is a line plot showing the transition of the molecular weight of the organic binder contained in the kneaded clay of Example 1.

Table 2 shows measurement results of the T1 relaxation time and the T2 relaxation time of the proton contained in the contained materials in the kneaded clay of Example 1 before kneading, at time points at intervals of 10 minutes during kneading, and after kneading. FIG. 4 shows the transition of the T1 relaxation time of the proton contained in the contained materials in the kneaded clay of Example 1 by a line plot, and FIG. 5 shows the transition of the T2 relaxation time of the proton contained in the contained materials in the kneaded clay of Example 1 by a line plot.

TABLE 2

(Test 1)

| | Kneading time (min.) | | | | | |
|---|---|---|---|---|---|---|
| | 0 | 10 | 20 | 30 | 40 | 50 |
| T1 relaxation time (m sec.) | 54 | 44.5 | 39 | 37 | 36.1 | 34.4 |
| T2 relaxation time (m sec.) | 11.7 | 7.9 | 7 | 6.7 | 6.6 | 6.1 |

Example 1

Magnetostatic Field Intensity of 0.3 T

With the passage of the kneading time, the T1 relaxation time and the T2 relaxation time of the proton contained in the contained materials in the kneaded clay were shortened. In particular, the line plots of FIGS. 4 and 5 showed the tendency of gradual decrease of the T1 relaxation time and the T2 relaxation time from 10 minutes to 20 minutes after the start of kneading, that is, the tendency of getting nearly horizontally. The change in the degree of decrease of the T1 relaxation time and the T2 relaxation time corresponded with the change of kneaded clay from a powdery form to a clayey form, which can be observed visually from 10 minutes to 20 minutes after the start of kneading.

3-2-3. State of Organic Binder:

The kneaded clay before kneading, 10 minutes, 20 minutes, 30 minutes, and 40 minutes after the start of kneading, and 50 minutes after the start of kneading (right after the completion of kneading) in the step of (2) of Example 1 was measured for the molecular weight of an organic binder contained in the kneaded clay.

Regarding the kneaded clay of Example 1, the kneading time and the molecular weight of an organic binder contained in the kneaded clay are shown in Tables 3 and 6. Incidentally, the molecular weight of the organic binder is shown as a standardized value.

TABLE 3

(Test 1)

| Kneading time (min.) | Molecular weight of organic binder |
|---|---|
| 0 | 1.00 |
| 10 | 0.92 |
| 20 | 0.46 |
| 30 | 0.32 |
| 40 | 0.26 |
| 50 | 0.21 |

The molecular weight of the organic binder drastically decreased from 10 minutes to 20 minutes after the start of kneading. This decrease in the molecular weight of the organic binder corresponds with the change of kneaded clay from a powdery form to a clayey form.

3-2-4. Extrusion Resistance:

The kneaded clay before kneading, 10 minutes, 20 minutes, 30 minutes, and 40 minutes after the start of kneading, and 50 minutes after the start of kneading (right after the completion of kneading) in the step of (2) of Example 1 was subjected to extrusion. Further, upon extrusion, the extrusion resistance was measured by the aforementioned measurement method.

Figure 7:
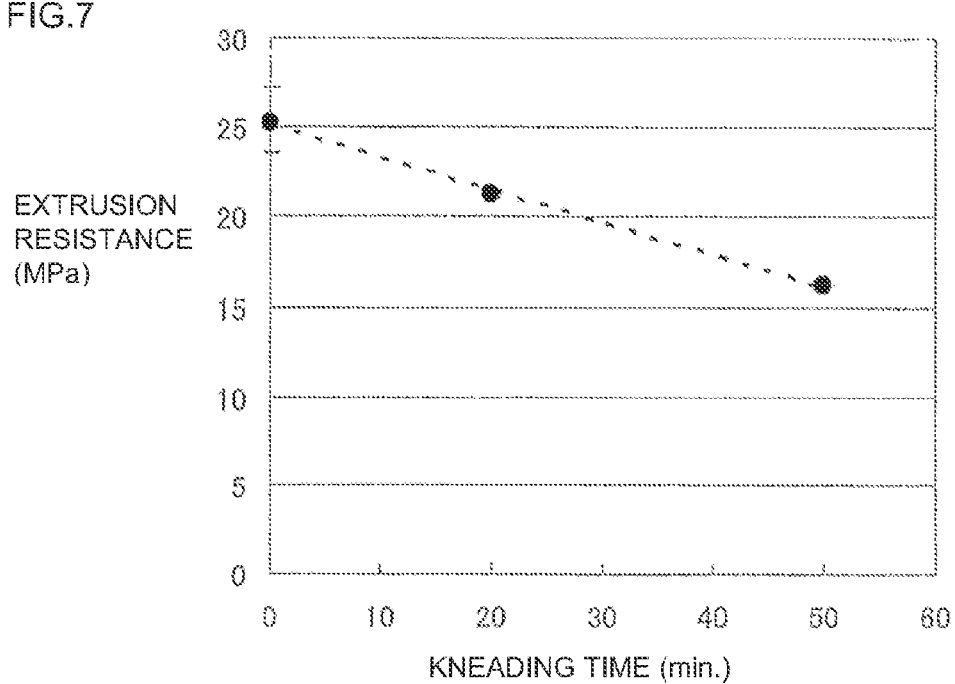
FIG. 7 is a line plot showing the relation between the kneading time and the extrusion resistance upon extrusion of the kneaded clay of Example 1.

FIG. 7 shows a line plot showing the relation between the kneading time and the extrusion resistance upon extrusion of the kneaded clay of Example 1.

It was found out that the extrusion resistance of the kneaded clay decreases with the passage of time.

3-3. Evaluation Test of the Relation Between Water Content and T1 and T2 Relaxation Times (Test 2):

Regarding Examples 2 to 5, where only the water content was different, the kneaded clay collected 50 minutes after the start of kneading was measured for the T1 relaxation time and the T2 relaxation time of the proton contained in the contained materials in the kneaded clay. Incidentally, the magnetostatic field intensity was 0.3 T.

Figure 8:
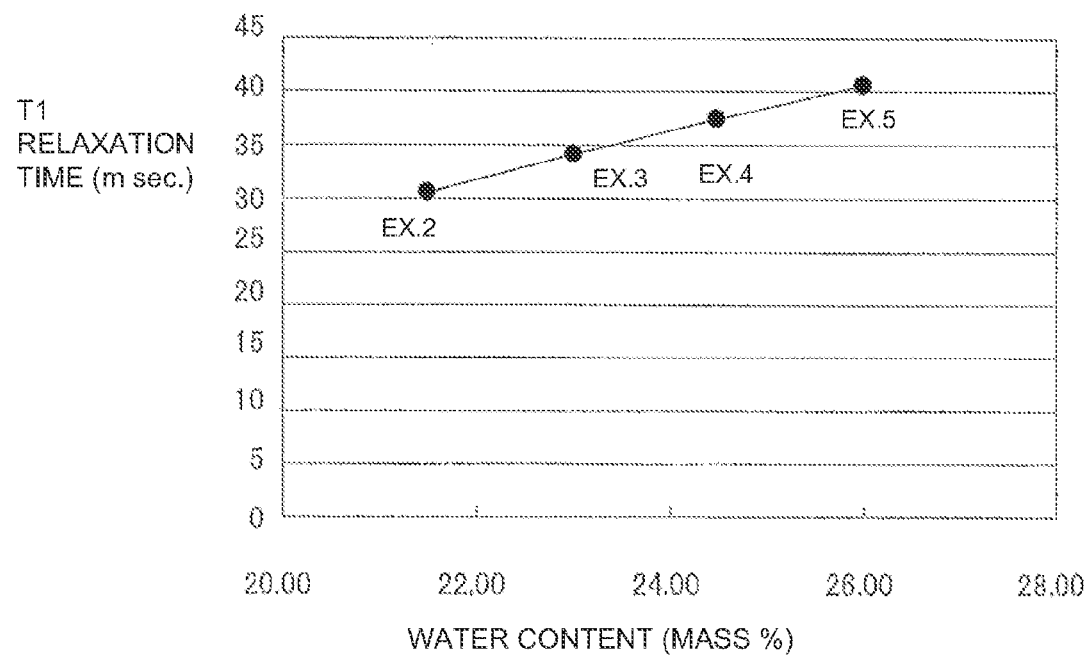
FIG. 8 is a line plot showing the relation between water content and the T1 relaxation time of the proton in the kneaded clay prepared in Examples 2 to 5.
Figure 9:
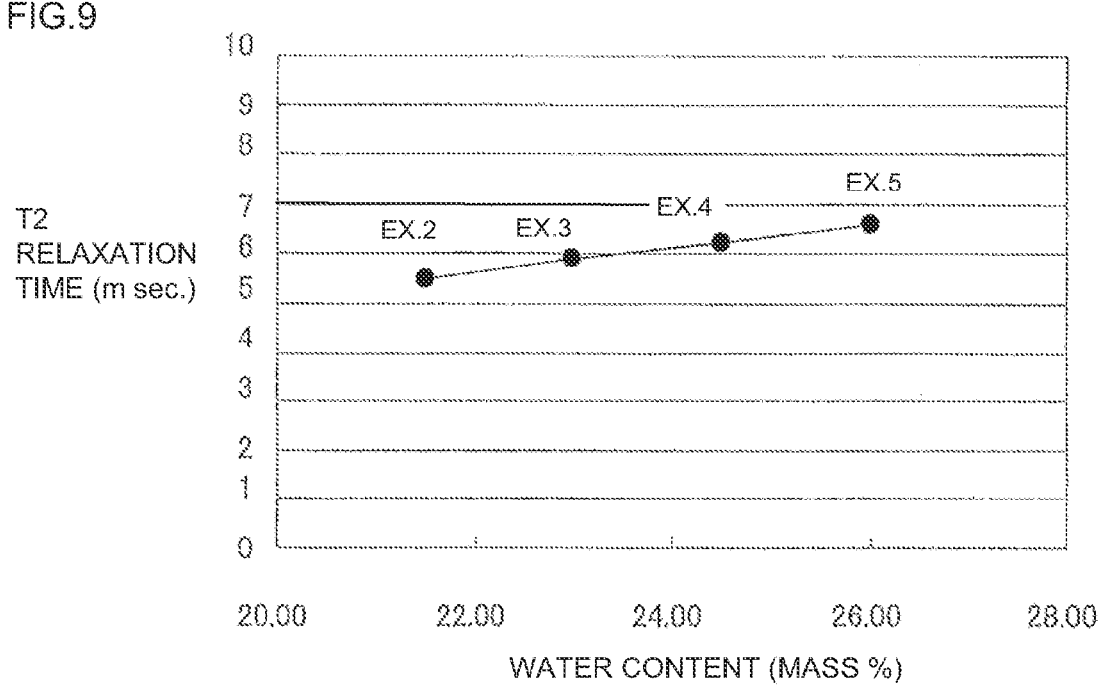
FIG. 9 is a line plot showing the relation between water content and the T2 relaxation time of the proton in the kneaded clay prepared in Examples 2 to 5.

Table 4 shows the measurement results of the T1 relaxation time and the T2 relaxation time of the proton contained in the contained materials in the kneaded clay collected 50 minutes after the start of kneading. Further, the T1 relaxation time of the proton contained in the contained materials in the kneaded clay of each of Examples 2 to 5 is shown in FIG. 8 by a line plot, and the T2 relaxation time of the same is shown in FIG. 9 by a line plot.

TABLE 4

(Test 2)

|  | T1 relaxation time (m sec.) | T2 relaxation time (m sec.) |
| --- | --- | --- |
| Example 2 | 30.5 | 5.5 |
| Example 3 | 34.1 | 5.9 |
| Example 4 | 37.4 | 6.2 |
| Example 5 | 40.6 | 6.6 |

The higher the water content is, the longer the T1 relaxation time and the T2 relaxation time of the proton contained in the contained materials in the kneaded clay are. It can be considered that, in the case that the water content was high, even when water completely covered the surfaces of ceramic raw material particles by kneading, a large number of remaining water molecules was present in a free state without being bonded to the surfaces of the particles.

3-4. Evaluation Test of the Relation Between Amounts of Organic Binder and Surfactant and T1 and T2 Relaxation Times (Test 3):

Regarding Examples 6 to 8, where only proportions of the organic binder and the surfactant were different, the kneaded clay collected 10 minutes, 20 minutes, and 30 minutes after the start of kneading was measured for the T1 relaxation time and the T2 relaxation time of the proton contained in the contained materials in the kneaded clay. Incidentally, in addition to the measurement with a magnetostatic field intensity of 0.3 T with regard to all of Examples 6 to 8, measurement with a magnetostatic field intensity of 9.4 T was performed with regard to Example 6.

Figure 10:
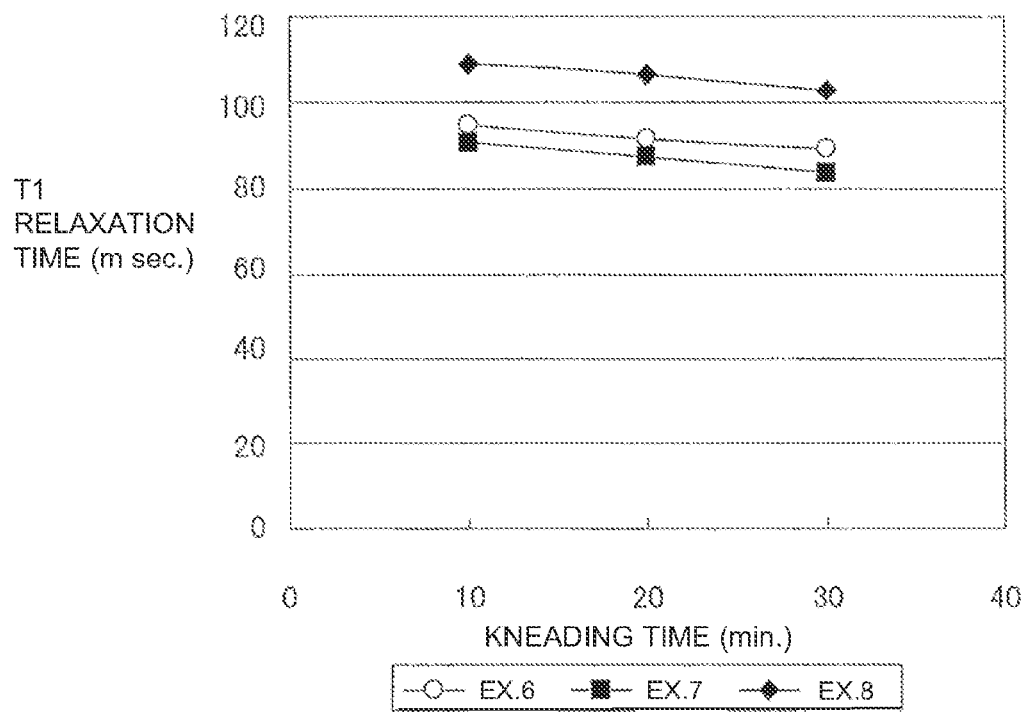
FIG. 10 is a line plot showing the transition of the T1 relaxation time of the proton contained in the contained materials in the kneaded clay of Examples 6 to 8.
Figure 11:
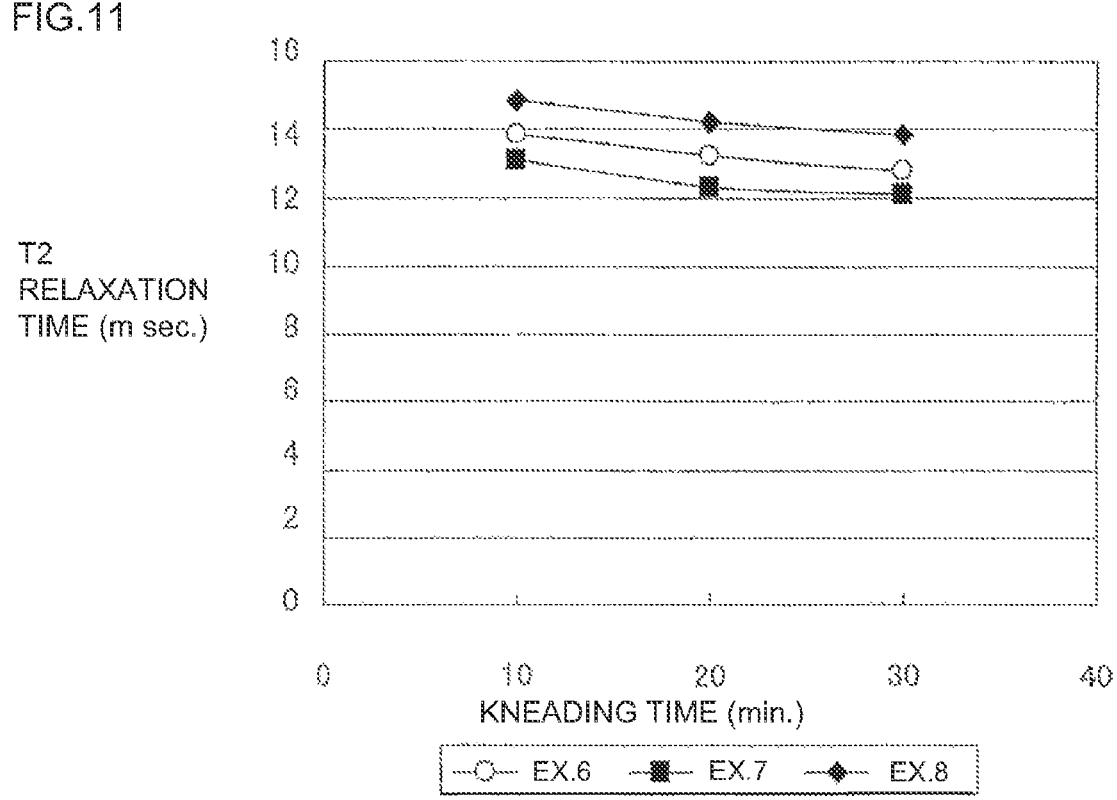
FIG. 11 is a line plot showing the transition of the T2 relaxation time of the proton contained in the contained materials in the kneaded clay of Examples 6 to 8.

Regarding the results of the measurement of the kneaded clay of each of Examples 6 to 8 for the T1 relaxation time and the T2 relaxation time of the proton contained in the contained materials in the kneaded clay 10 minutes, 20 minutes, and 30 minutes after the start of kneading, the results of Examples 6 and 7 measured with a magnetostatic field intensity of 0.3 T are shown in Table 5, and the results of Example 6 measured with a magnetostatic field intensity of 9.4 T are shown in Table 6. Further, the transition of the T1 relaxation time of the proton contained in the contained materials in the kneaded clay in each of Examples 6 and 7 measured with a magnetostatic field intensity of 0.3 T is shown in FIG. 10 by a line plot, and the transition of the T2 relaxation time of the same is shown in FIG. 11 by a line plot.

TABLE 5

(Test 3)

|  | Example 6 | | | Example 7 | | | Example 8 | | |
| --- | --- | --- | --- | --- | --- | --- | --- | --- | --- |
| Kneading time (min.) | 10 | 20 | 30 | 10 | 20 | 30 | 10 | 20 | 30 |
| T1 relaxation time (m sec.) | 94.7 | 91.6 | 89.1 | 90.5 | 87.3 | 83.6 | 108.6 | 106.3 | 102.8 |
| T2 relaxation time (m sec.) | 13.8 | 13.2 | 12.8 | 13.1 | 12.3 | 12.1 | 14.8 | 14.2 | 13.8 |

Magnetostatic field intensity of 0.3 T

TABLE 6

(Test 3)

|  | Example 6 | | |
| --- | --- | --- | --- |
| Kneading time (min.) | 10 | 20 | 30 |
| T1 relaxation time (m sec.) | 652.1 | 601.0 | 561.7 |
| T2 relaxation time (m sec.) | 1.63 | 1.52 | 1.50 |

Magnetostatic field intensity of 9.4 T

It was found out that, when the organic binder content and the surfactant content are different, the T1 relaxation time and the T2 relaxation time of the proton contained in the contained materials of the kneaded clay are different. In addition, the T1 relaxation time and the T2 relaxation time of the proton contained in the contained materials of the kneaded clay of Example 6 remarkably differ between the magnetostatic field intensity of 0.3 T and the magnetostatic field intensity of 9.4 T. This means the relaxation times of the proton changes depending on the magnetostatic field intensity, that is, depending on the specifications of the measurement device. That is, it means that the state of kneading of kneaded clay cannot be recognized strictly by the absolute value of the relaxation time. In addition, when the magnetostatic field intensity is high, the T1 relaxation time tends to be long, and, when the magnetostatic field intensity is low, the T2 relaxation time tends to be long. For example, even in the case of the kneaded clay having almost the same measurement value of the T1 relaxation time at the magnetostatic field intensity of 0.3 T, it may have a possibility of showing a significant different in the T1 relaxation time at the magnetostatic field intensity of 9.4 T. That is, it suggests that even a slight difference in the nature of kneaded clay can be recognized by measuring the T1 relaxation time and the T2 relaxation time by changing the magnetostatic field intensity.

The present invention can be used as a method for evaluating kneaded clay used for manufacturing a ceramic structure used for a filter, a catalyst carrier, an electric transmission insulator, a refractory, or the like and an a method for manufacturing kneaded clay.

What is claimed is:

1. A method of evaluating kneaded clay which comprises:
preparing kneaded clay by mixing and kneading at least ceramic raw material and water as contained materials,
measuring at least one of T1 relaxation time and T2 relaxation time of a proton in the contained materials by an NMR method, and
evaluating a kneaded state of the kneaded clay to determine whether the water covers surfaces of the ceramic raw material in a membrane state.

2. A method for evaluating kneaded clay according to claim 1, wherein a signal for measuring the at least one of T1 relaxation time and the T2 relaxation time of the proton contained in the contained materials has the signal sent from the proton of the water as the main component.

3. A method for evaluating kneaded clay according to claim 1, wherein the kneaded clay is for subjecting, after the kneading, to a forming step, a drying step, and a firing step.

4. A method for evaluating kneaded clay according to claim 3, wherein the kneaded clay has one of a cordierite composition and an alumina composition after the firing step.

5. A method for manufacturing kneaded clay which comprises: using a method for evaluating kneaded clay according to claim 1, and kneading the kneaded clay while checking the kneaded state of the kneaded clay by at least one of the T1 relaxation time and the T2 relaxation time of the proton contained in the contained materials.

6. A method for manufacturing kneaded clay which comprises: using a method for evaluating kneaded clay according to claim 2, and kneading the kneaded clay while checking the kneaded state of the kneaded clay by at least one of the T1 relaxation time and the T2 relaxation time of the proton contained in the contained materials.

7. A method for manufacturing kneaded clay comprising:
preparing kneaded clay by mixing and kneading at least ceramic raw material and water as contained materials,
measuring at least one of T1 relaxation time and T2 relaxation time of a proton in the contained materials by an NMR method,
kneading the kneaded clay while checking the kneaded state of the kneaded clay by the at least one T1 relaxation time and the T2 relaxation time of the proton contained in the contained materials, and
evaluating a kneaded state of the kneaded clay to determine whether the water covers surfaces of the ceramic raw material in a membrane state,
wherein the kneaded clay is kneaded until the T1 relaxation time, measured at magnetostatic field strength of 0.3 to 9.4 T, of the proton contained in the contained materials becomes 80% or less of the initial value before kneading.

* * * * *